US00PP14153P29

(12) United States Plant Patent
Smith

(10) Patent No.: US PP14,153 P2
(45) Date of Patent: Sep. 23, 2003

(54) CHRYSANTHEMUM PLANT NAMED 'DREAMY YOLYNN'

(75) Inventor: Mark A. Smith, Fort Myers, FL (US)

(73) Assignee: Yoder Brothers, Inc., Barberton, OH (US)

( * ) Notice: Subject to any disclaimer, the term of this patent is extended or adjusted under 35 U.S.C. 154(b) by 31 days.

(21) Appl. No.: 10/094,279

(22) Filed: Mar. 8, 2002

(51) Int. Cl.[7] ..... A01H 5/00

(52) U.S. Cl. ..... Plt./289

(58) Field of Search ..... Plt./289, 295

*Primary Examiner*—Bruce R. Campell
*Assistant Examiner*—Annette Para
(74) *Attorney, Agent, or Firm*—C. A. Whealy

(57) ABSTRACT

A distinct cultivar of Chrysanthemum plant named 'Dreamy Yolynn', characterized by its upright and mounded plant habit; freely branching habit; uniform and freely flowering habit; decorative-type inflorescences; creamy yellow-colored ray florets; and natural season flowering in early October in the Northern Hemisphere.

1 Drawing Sheet

BOTANICAL CLASSIFICATION/CULTIVAR DESIGNATION

*Chrysanthemum×morifolium* cultivar Dreamy Yolynn.

BACKGROUND OF THE INVENTION

The present invention relates to a new and distinct cultivar of Chrysanthemum plant, botanically known as *Chrysanthemum×morifolium*, commercially known as a garden-type Chrysanthemum and hereinafter referred to by the name 'Dreamy Yolynn'.

The new cultivar is a product of a mutation induction program conducted by the Inventor in Fort Myers, Fla. The objective of the program is to create new garden-type Chrysanthemum cultivars having inflorescences with desirable inflorescence forms, attractive floret colors and good garden performance.

The new Chrysanthemum originated by exposing unrooted cuttings of the Chrysanthemum cultivar Peachy Lynn, disclosed in U.S. Plant Pat. No. 8,892, to X-ray radiation in July, 1998 in Fort Myers, Fla. Following the radiation treatment, the cuttings were rooted and terminal apices were removed (pinched) three times to promote lateral branch development. After lateral branches from the third pinch reached sufficient size, terminal cuttings were harvested, planted and flowered in a controlled environment in Fort Myers, Fla. The new Chrysanthemum was discovered and selected by the Inventor as a single flowering plant within this population in January, 1999. The selection of this plant was based on its desirable inflorescence form, attractive ray floret color and good garden performance.

Asexual reproduction of the new cultivar by terminal cuttings taken in a controlled environment in Fort Myers, Fla. since March, 1999, has shown that the unique features of this new Chrysanthemum are stable and reproduced true to type in successive generations.

SUMMARY OF THE INVENTION

The cultivar Dreamy Yolynn has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Dreamy Yolynn'. These characteristics in combination distinguish 'Dreamy Yolynn' as a new and distinct cultivar:

1. Upright and mounded plant habit.
2. Freely branching habit; dense and full plants.
3. Uniform and freely flowering habit.
4. Decorative-type inflorescences.
5. Creamy yellow-colored ray florets.
6. Natural season flowering in early October in the Northern Hemisphere.

Plants of the new Chrysanthemum are most similar to plants of the the cultivar Peachy Lynn. In side-by-side comparisons conducted in Fort Myers, Fla., plants of the new Chrysanthemum differed from plants of the cultivar Peachy Lynn primarily in ray floret coloration as ray florets of the cultivar Peachy Lynn are coral in color.

Plants of the new Chrysanthemum can be compared to plants of the the cultivar Lynn, disclosed in U.S. Plant Pat. No. 8,171. In side-by-side comparisons conducted in Fort Myers, Fla., plants of the new Chrysanthemum differed from plants of the cultivar Lynn in the following characteristics:

1. Plants of the new Chrysanthemum flowered about one week earlier than plants of the cultivar Lynn when flowered under natural season conditions.
2. Ray florets of the new Chrysanthemum and the cultivar Lynn differed in ray floret color as ray florets of the cultivar Lynn were light purple.

BRIEF DESCRIPTION OF THE PHOTOGRAPHS

The accompanying photographs illustrate the overall appearance of the new Chrysanthemum. These photographs show the colors as true as it is reasonably possible to obtain in colored reproductions of this type. Colors in the photographs may differ slightly from the color values cited in the detailed botanical description which accurately describe the colors of the new Chrysanthemum.

The photograph at the top of the sheet comprises a side perspective view of a typical flowering plant of 'Dreamy Yolynn'.

The photograph at the bottom of the sheet comprises a close-up view of typical inflorescences of the cultivar 'Dreamy Yolynn'.

DETAILED BOTANICAL DESCRIPTION

In the following description, color references are made to The Royal Horticultural Society Colour Chart, 1995 Edition, except where general terms of ordinary dictionary significance are used. The following observations and measurements describe plants grown in an outdoor nursery in Pendleton, S.C., under natural season conditions and practices which approximate those generally used in commercial garden-type Chrysanthemum production. One rooted cutting was planted in a 16.5-cm container in late July, 2002. Plants were not pinched, that is, the terminal apex was not removed to enhance branching. During the production of the plants, day temperatures ranged from 29 to 32° C. and night temperatures ranged from 16 to 21° C. Measurements and numerical values represent averages for typical flowering plants.

Botanical classification: *Chrysanthemum×morifolium* cultivar Dreamy Yolynn.

Commercial classification: Decorative-type garden Chrysanthemum.

Parentage: Induced mutation of the *Chrysanthemum×morifolium* cultivar Peachy Lynn, disclosed in U.S. Plant Pat. No. 8,892.

Propagation:

*Type.*—Terminal tip cuttings.

*Time to initiate roots.*—About four days at 21° C.

*Time to produce a rooted cutting.*—About ten days at 21° C.

*Root description.*—White, fine and fibrous.

*Rooting habit.*—Freely branching.

Plant description:

*Appearance.*—Perennial herbaceous decorative-type garden Chrysanthemum. Inverted triangle. Stems initially upright, then somewhat outwardly spreading giving a uniformly mounded appearance to the plant. Freely branching with lateral branches forming at every node.

*Plant height.*—About 22.5 cm.

*Plant diameter.*—About 37 cm.

*Lateral branches.*—Length: About 20 cm. Diameter: About 5 mm. Internode length: About 1.4 cm. Aspect: Upright and outwardly spreading. Texture: Pubescent. Color: 144A to 146A.

*Foliage description.*—Leaf arrangement: Alternate. Length: About 3.4 cm. Width: About 2.75 cm. Apex: Cuspidate to mucronate. Base: Attenuate. Margin: Palmately lobed, sinuses mostly divergent. Texture: Both surfaces, pubescent; veins prominent on lower surface. Color: Young and mature foliage upper surface: Slightly darker than 147A. Young and mature foliage lower surface: Darker than 147B. Venation, upper surface: 147B. Venation, lower surface: 147B to 147C. Petiole length: About 4 mm. Petiole diameter: About 3 mm. Petiole color, both surfaces: Close to 146B.

Inflorescence description:

*Appearance.*—Decorative-type inflorescence form with elongated oblong-shaped ray florets. Inflorescences borne on terminals above foliage, arising from leaf axils. Disk and ray florets arranged acropetally on a capitulum. About 7 inflorescences per lateral.

*Flowering response.*—Under natural season conditions, plants flower in early October in the Northern Hemisphere and continue to flower for at least three weeks depending on weather conditions.

*Inflorescence bud (before showing color).*—Height: About 4 mm. Diameter: About 6 mm. Phyllary color: Darker than 143A.

*Inflorescence size.*—Diameter: About 4.5 cm. Depth (height): About 1.75 cm. Disc diameter: About 4 mm or less, inconspicuous. Receptacle diameter: About 6 mm.

*Ray florets.*—Shape: Elongated oblong. Length: About 2.2 cm. Corolla tube length: About 3 mm. Width: About 6 mm. Apex: Rounded or acute. Margin: Entire. Texture: Smooth, glabrous, satiny. Surface: Concave to flat. Orientation: Initially upright and incurved, then perpendicular to the peduncle. Number of ray florets per inflorescence: About 225. Color: When opening, upper and lower surfaces: Close to 5A. Opened inflorescence, upper surface: Close to 5D; fading to 4D with subsequent development. Opened inflorescence, lower surface: Close to 5D to 4D.

*Disc florets.*—Shape: Tubular, apex dentate. Length: About 6 mm. Width: Apex: About 1.5 mm. Base: About 1 mm. Number of disc florets per inflorescence: Less than 20. Color: Immature: 154A to 9A. Mature: Apex: 9A to 12A. Mid-section: 154D. Base: 155D.

*Peduncle.*—Aspect: Flexible, angled about 45° from the stem. Length: First peduncle: About 5.1 cm. Fourth peduncle: About 7.4 cm. Diameter: About 2 mm. Texture: Pubescent. Color: 144A to 146A.

*Reproductive organs.*—Androecium: Present on disc florets only. Anther color: 12A. Pollen: Moderate. Pollen color: 15A. Gynoecium: Present on both ray and disc florets.

*Seed.*—Seed production has not been observed.

Disease/pest resistance: Plants of the new Chrysanthemum have not been shown to be resistant to pathogens and pests common to Chrysanthemums.

Garden performance: Plants of the new Chrysanthemum have been observed to be tolerant to rain, wind and temperatures ranging from 0 to more than 40° C.

It is claimed:

1. A new and distinct cultivar of Chrysanthemum plant named 'Dreamy Yolynn', as illustrated and described.

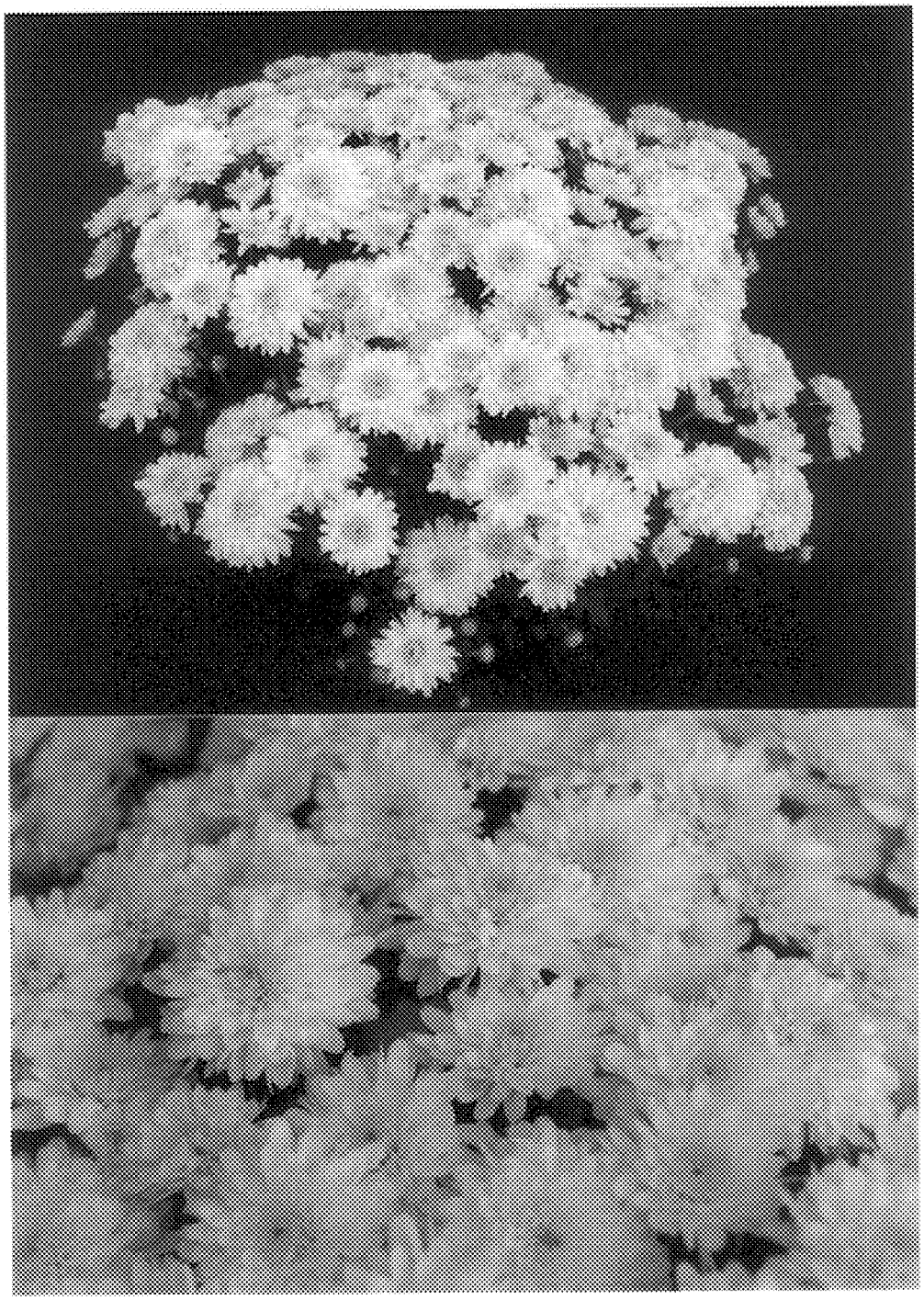

* * * * *